(12) United States Patent
Popescu et al.

(10) Patent No.: US 7,027,737 B2
(45) Date of Patent: Apr. 11, 2006

(54) METHOD AND APPARATUS FOR TRANSMITTING DATA FROM A ROTARY PART TO A STATIONARY PART OF A DATA GENERATING SYSTEM

(75) Inventors: Stefan Popescu, Erlangen (DE); Wolf-Ekkehard Blanz, Danville, CA (US)

(73) Assignee: Siemens Aktiengesellschaft, Munich (DE)

( * ) Notice: Subject to any disclaimer, the term of this patent is extended or adjusted under 35 U.S.C. 154(b) by 722 days.

(21) Appl. No.: 10/255,976

(22) Filed: Sep. 26, 2002

(65) Prior Publication Data

US 2004/0062344 A1   Apr. 1, 2004

(51) Int. Cl.
*H04B 10/00* (2006.01)

(52) U.S. Cl. ............... 398/114; 398/106; 385/15
(58) Field of Classification Search ........... 398/114, 398/106; 378/15
See application file for complete search history.

(56) References Cited

U.S. PATENT DOCUMENTS

| | | | |
|---|---|---|---|
| 4,259,584 A | | 3/1981 | Krumme |
| 4,529,584 A | * | 7/1985 | Mulvey et al. ............... 424/52 |
| 4,555,631 A | * | 11/1985 | Martens ....................... 250/551 |
| 4,794,796 A | | 1/1989 | Mitchell |
| 4,796,183 A | | 1/1989 | Ermert et al. |
| 4,996,435 A | | 2/1991 | Keller |
| 5,134,169 A | * | 7/1992 | Green et al. .................. 521/25 |
| 5,134,639 A | | 7/1992 | Vekstein et al. |
| 5,140,696 A | | 8/1992 | Fox |
| 5,229,871 A | * | 7/1993 | Czarnek et al. ............... 359/15 |
| 5,469,488 A | * | 11/1995 | Ono ........................... 378/15 |
| 5,535,033 A | * | 7/1996 | Guempelein et al. ....... 398/114 |
| 6,043,916 A | * | 3/2000 | Poisel et al. ................ 398/114 |

* cited by examiner

*Primary Examiner*—Jason Chan
*Assistant Examiner*—Ken Malkowski
(74) *Attorney, Agent, or Firm*—Schiff Hardin LLP

(57) ABSTRACT

In a method and an arrangement for transmitting data from a rotary part to a stationary part of a system, a light-transmitting channel is formed by an optically reflecting half channel in the stationary part and an optically reflecting half channel in the rotary part, facing each other, with each half channel having a parabolic cross-section and with the half channels being oriented so that the respective focal points and the respective vertices of the two half channels are co-linear. A light emitter is supplied with data to be transmitted and is disposed in the wall of the half channel in the rotary part, and emits modulated light representing the data into the light channel in two opposite directions. At least one of these light beams is detected by a light detector disposed in the wall of the half channel in the stationary part, and the data in the detected beam is then made available for transmission from the stationary part. A light barrier is disposed in the light channel to, generally, block one of the light beams so that, generally, only one beam at a time is detected by the light detectors.

23 Claims, 3 Drawing Sheets

METHOD AND APPARATUS FOR TRANSMITTING DATA FROM A ROTARY PART TO A STATIONARY PART OF A DATA GENERATING SYSTEM

BACKGROUND OF THE INVENTION

1. Field of the Invention

The present invention is directed to a method as well as to an apparatus for transmitting data from a rotating part to a stationary part of a system wherein data are generated, and in particular to such a method and apparatus for transmitting data representing radiation attenuation values obtained in a computer tomography (CT) apparatus while rotating a live ring relative to a stationary frame, wherein the data are transmitted from the stationary frame to a computer for generating an image.

2. Description of the Prior Art

Computed tomography (CT) systems are a well-known imaging modality wherein a rotary part, known as a live ring or gantry, carries a measurement system which is rotated around a rotational axis relative to a stationary part of the apparatus. The measurement system typically is formed by an X-ray source and a radiation detector. Power is supplied from the stationary part to the components on the rotary part, typically via slip rings, and the rotary part continuously revolves while X-ray measurement data are being generated and transmitted to the stationary part. The data are typically transmitted from the stationary part to a computer wherein an image of an examination subject, around whom the measurement system rotated, is reconstructed.

A recent development in computed tomography are multi-slice CT systems, which generate larger amounts of data which must be transmitted in a shorter time between the measurement system and the image reconstruction system. For example, a four-slices CT system rotating with a maximum of 120 rot/min requires a data link with a capacity of approximately 200 MBaud. Increasing the number of slices to 16 with the same rotational speed increases the required transmission rate to 800 MBaud. The transmission rate can exceed 1 GBaud if the system rotates even faster. Transferring such data in real time at this rate between the rotary part and the stationary part is difficult to implement with conventional techniques.

Conventional computed tomography systems which do not require such a high transmission rate have employed baseband transmission between a rotating transmitting antenna, formed in strip-line technology, and a stationary receiving antenna mounted relatively close to the transmitting antenna. Such a system is described, for example, in U.S. Pat. No. 5,140,696. In a variation of this conventional arrangement, U.S. Pat. Nos. 4,794,796 and 4,796,183describe systems wherein data are transmitted from a rotary part to a stationary part via a rotating waveguide.

These conventional techniques becomes increasingly difficult to implement when the data transmission rate reaches the GHz range, because the wavelength becomes shorter, and the spacing between the rotary part and the stationary part is then comparable to a quarter of the wavelength. With shorter wavelengths the requirements for mechanical precision and alignment of components become more critical, thereby increasing the overall cost. Moreover, as the data rate increases it becomes more difficult to address the electromatic compatibility (EMC) problems associated both with limiting parasitic radiation and providing immunity to external perturbations.

In recognition of these problems associated with broadband transmission, modulated light has been employed as an alternative transmission medium. Systems employing modulated light for this purpose can be categorized as four basic types, as follows.

In a first approach, a number of rotating light sources are used, which emit overlapping light beams which propagate toward one or more stationary light receivers. For example, U.S. Pat. No. 4,996,435 discloses an optical system for transmitting data between a stationary part and a rotary part having a number of light transmitters arranged on a circle on one of the parts, with a single light receiver disposed on the other part. U.S. Pat. No. 5,229,871 discloses an optical data link for communicating data between a stationary member and rotary member, and an X-ray computed tomography apparatus incorporating such an optical data link, wherein one or more transmitters are used with a single receiver, with elliptical reflectors to maximize the light captured by the receiver. U.S. Pat. No. 5,469,488 discloses an X-ray computed tomography scanner having a number of light-emitting elements and a light-receiving element, with a light collector to converge the light to the receiver.

A typical computed tomography apparatus has a gantry with a relatively large diameter, of approximately 1.5 m. A disadvantage of systems of this first type when employed in such a computed tomography apparatus is that, in the GBaud range of data transmission, the bit duration is less than 1 ns, whereas the signal propagation speed in air is about 3 ns/m. This means that the transmitted signal will be delayed by respectively different amounts from different transmitters on the rotary part relative to the stationary receiver, and this difference is larger than the bit duration and therefore leads to mode divergence and pulse widening. This makes this first approach inappropriate for transmitting data at high rates.

A second known approach is to rotate a modulated light source with the rotary part, and to laterally couple the modulated light into a stationary optical fiber ring. A light receiver is axially coupled to the optical fiber.

This approach is exemplified by German PS 44 21 616, as well as U.S. Pat. No. 6,043,916. In U.S. Pat. No. 6,043,916, a single light emitter is used to transmit the informational signal, and the receiver is a fluorescing fiber optic connection which proceeds within a circular ring configuration, and which has at least one detector mounted at or near at least one of the fibers. The emitter emits the informational signals into the fluorescing fiber optic connection at an angle which is approximately perpendicular to the center axis of the fiber.

A disadvantage of this second known approach is the very limited efficiency of coupling light laterally into the optical fiber. The aforementioned use of fluorescent fiber material improves the coupling, however, the fluorescent effect is relatively slow, and thus limits the light's modulation rate, and thus also limits the maximum data transmission rate. In practice, the rate is limited to approximately 100 MBaud with such a fluorescent optical fiber. It is also known to use plastic (i.e., non-fluorescing) fiber with a special cladding to allow light to be injected into the fiber directly from the exterior into the fiber's core. The coupling efficiency, however, is still very low, and the propagation attenuation for the light within the plastic fiber is very high.

In a third known approach, modulated light from a rotating light source is injected axially into a rotating optical fiber ring. A stationary light receiver detects light that is laterally emitted along the entire fiber length.

An example of this technique is disclosed in U.S. Pat. No. 5,535,033 wherein the optical conductor is formed by a bundle of optical fibers having transparent cladding, so that the optical conductor laterally emits light along its entire length corresponding to the data signals which were coupled into the optical conductor.

Another example of this technique is disclosed in U.S. Pat. No. 4,259,584, wherein a ring of light-conductive material is curved around the center of rotation of a rotary part, and light is emitted onto the surface of this material. The light propagates in the conductive ring substantially along the entire length thereof, and the ring has at least one point at which it is interrupted, at which a light receiver is disposed.

A disadvantage of this third known approach is the high attenuation of the signal along the fiber, both due to core loss and lateral emission. Only plastic fibers with an exposed core can be used, so that the attenuation along the plastic fiber is very high. Further, light attenuation increases exponentially along the plastic fiber because of lateral emission. Because of these disadvantages, this third approach is unsuitable for consideration for use with higher data transmission rates.

A fourth known approach is to form a hollow light channel of one channel half in the rotary part and another channel half in the stationary part with the two channel halves facing each other. Modulated light carrying the data is transmitted from the location of a light emitter to the location of a light detector or receiver with several reflections off of the walls of the light channel occurring therebetween.

A system of this type is described in U.S. Pat. No. 4,555,631, which employs only a single reflecting surface in the form of a hollow cylinder with a mirror interior surface. The light source produces two light beams circulating in opposite directions inside the hollow cylinder, with multiple reflections occurring on the interior cylindrical surface until the light beams eventually exit the cylinder via an escape window, toward the light detector. This system is intended to reduce light attenuation by minimizing the number of reflections between the light source and the light detector, by using the smallest possible grazing angle of the light beam on the interior surface of the cylinder. The use of a small grazing angle, however, means that the launch angle for the light emitted from the light source must be very close to the tangent of the cylindrical surface. This means that the light will be reflected multiple times as it propagates along the circular cross-section of the cylinder until it reaches the detector. Another disadvantage of this known system is that the light detector must be preceded by a relatively complicated and precise optical system, so as to capture the light which emerges almost tangentially, and in both directions, from the cylinder, depending on the relative position between the light source and the escape window. Moreover, the light inside the cylinder follows a polygonal path that rotates together with the light source. Therefore, vertices of the polygonal path are moving on the cylinder surface relative to the capture window, and the light emerging through this window therefore will have a variable intensity and a variable angle of incidence, which complicates the structure and circuitry of the light receiver. In order to catch enough light at the light detector during continuous rotation, moreover, the light beam must be of a relatively large diameter, which increases the mode dispersion and leads to pulse widening.

Another system employing this fourth approach has an arcuate hollow light conductor with reflecting interior walls, with a rectangular cross-section. The light conductor has one-half or part that rotates with the rotary part of the gantry, and another part or half that is fixed to the stator of the gantry. Light beams carrying data are transmitted into this conductor, and are subsequently extracted therefrom after propagating through at least portion of the conductor.

The system disclosed in U.S. Pat. No. 5,134,639 has several disadvantages. There is no discussion therein as to how to address the high dynamic range of the received signal due to losses caused by dispersion and reflections. Additionally, the rectangular-shaped cross-section must be very precisely structured, in order to reduce light scattering. Without such a precise structure, light attenuation is very high because the light may be reflected outside of the hollow conductor through an unwanted gap between the rotating and stationary parts. Additionally, this known system uses a highly divergent light source (LED) that increases the light dispersion, as well as increasing the mode interference, due to the fact that the light rays within the beam bundle follow various and different paths of different lengths, and thus exhibit different propagation times. The data transmission rate of this known system, therefore is limited to approximately 10 MBaud.

One further arrangement is known from German OS 2 113 690, wherein a light conducting channel is formed by two facing half channels, one-half channel being formed in the rotary part and the other half channel being formed in the stationary part. These respective half channels have parabolic cross-sections, and thus each parabolic cross-section has a focal point. A light-emitting diode is disposed at the focal point of one of the parabolic half sections, and a photo detector is disposed at the focal point of the other half section.

SUMMARY OF THE INVENTION

It is an object of the present invention to provide a method and an arrangement for transmitting data from a rotary part to a stationary part of a system which allow the data to be transmitted accurately at a data transmission rate of at least 200 MBaud, thereby providing a method and an arrangement suitable for use in a four-slices CT system.

It is a further object of the present invention to provide such a method and arrangement which allow data to be accurately transmitted at data transmission rates exceeding 1 GBaud.

The above object is achieved in accordance with the principles of the present invention in a method and an arrangement for transmitting data from a rotary part to a stationary part of a system, wherein a light-transmitting channel is formed by an optically reflecting half channel in the stationary part and an optically reflecting half channel in the rotary part, facing each other, with each half channel having a parabolic cross-section and with the half channels being oriented so that the respective focal points and the respective vertices of the two half channels are co-linear. A light emitter is supplied with data to be transmitted and is disposed in the wall of the half channel in the rotary part, and emits modulated light representing the data into the light channel in two opposite directions. At least one of these light beams is detected by a light detector disposed in the wall of the half channel in the stationary part, and the data contained in the detected beam are then made available for transmission from the stationary part. A light barrier is disposed in the light channel to, generally, block one of the light beams so that, generally, only one beam at a time is detected by the light detectors.

Preferably at least one light barrier is disposed in the light channel, so that only one of the two light beams propagating in opposite directions will reach the detector. When the light emitter and the light detector are oriented at 180° relative to each other, however, both light beams may reach the detector, however, the light intensity at the detector will gradually and smoothly change as a function of the rotation angle, and thus the transmission in signal level will be smooth.

The parabolic cross-sectional shape of the two half channels, and the orientation of the two half channels with their focal points and vertices in linear alignment, minimizes light scattering and light attenuation due to light escaping from the channel through the gap between the rotary part and the stationary part. The mirrored interior walls of the two half channels and their parabolic cross-section cause any scattered light to converge back to a central region of the propagation path. This applies as well to light scatter due to surface defects in the two half channels.

In an embodiment one or more light absorber gaps are positioned at respective locations around the light channel. The respective positions of these light absorber gaps are selected to be equal to the respective wavelengths of undesired modes of propagation of the light, so that only certain light propagation modes are permitted. This reduces mode dispersion or pulse widening at the light detector, thereby contributing to achieving higher data transmission rates. The light emitter preferably emits a non-dispersing light beam and is, for example, a laser. The light detector is preferably formed as a photodiode array, with a monochromatic light filter and guide disposed in front of the array. The light emitter is disposed in a non-reflective cavity opening into a wall of the half channel disposed in the rotary part, and the light detector is disposed in a non-reflective cavity opening into the half channel disposed in the stationary part.

In order to emit the light in two directions into the light channel, the light emitter has a light source, such as the aforementioned laser, which emits a light beam that passes through a semi-transparent mirror, preferably with a 50% transparency, so that two beams of substantially equal intensity, proceeding in opposite directions, are emitted into the light channel.

DESCRIPTION OF THE PREFERRED EMBODIMENTS

Figure 1:
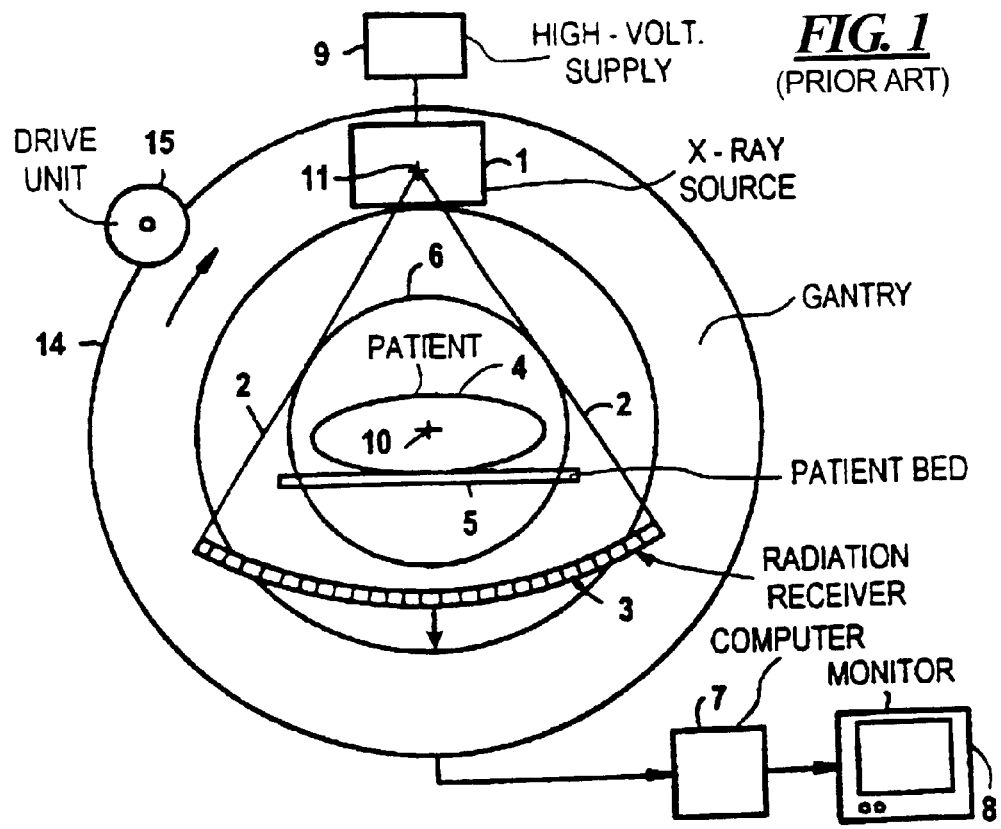
FIG. 1 schematically illustrates the basic components of a computed tomography apparatus in which an inventive data transmission arrangement, operating in accordance with the inventive method, can be incorporated.

The basic components of a known computed tomography (CT) system are shown in FIG. 1. The system has an X-ray source 1 which emits an X-ray beam from a focus 11. The margin rays 2 of the X-ray beam are indicated in FIG. 1. The X-ray beam strikes a radiation receiver or detector 3 after passing through a patient 4 disposed on a patient table 5 in an examination volume 6. Attenuation values generated by the radiation receiver 3 in a known manner are supplied to a computer 7 which, also in a known manner, reconstructs an image of the patient 4 therefrom, which is displayed on a monitor 8.

While the attenuation values are being obtained, the measurement system, formed by the X-ray source 1 and the radiation receiver 3, is rotated around a rotational axis 10 (which in the embodiment of FIG. 1 also is the system axis). For this purpose, the X-ray source 1 and the radiation receiver 3 are mounted on a rotary part 12 (see FIG. 2) of a gantry 14, which is driven by a drive unit 15. The rotary part 12 rotates relative to a stationary part 13 (see FIG. 2) of the gantry, which has a data output at which the attenuation values continuously arrive during a scan of the patient 4, for supply to the computer 7 in real time.

The radiation receiver 3 is composed of a number of rows of detector elements, thereby forming a multi-row detector for a multi-slice examination. As described above in such a multi-slice examination, when the rotary part 12 rotates at 120 rot/min, data are produced at a transmission rate of approximately 200 MBaud. In order to transmit data at this and higher transmission rates, an arrangement constructed and operating in accordance with the present invention is employed in the system shown in FIG. 1, as shown in FIGS. 2, 3 and 4.

Figure 2:
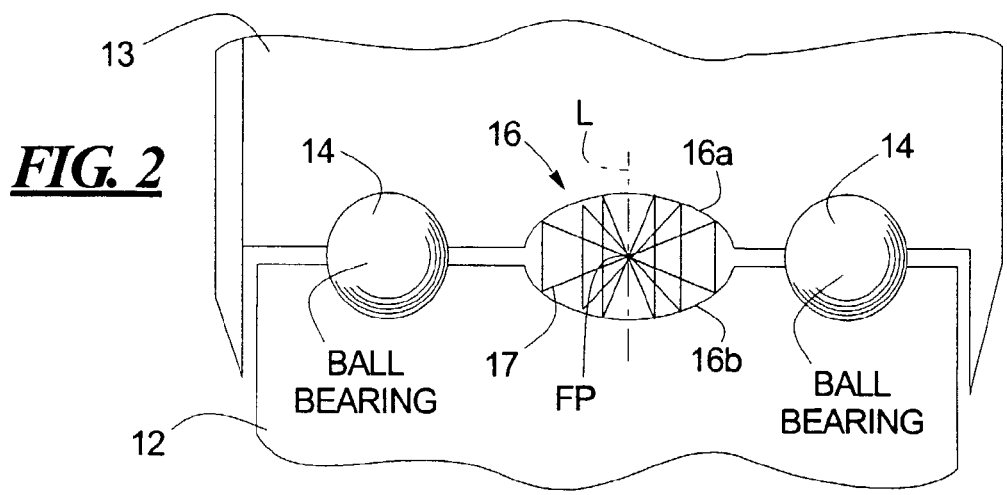
FIG. 2 is a sectional view through the gantry in the system shown in FIG. 1, taken in a plane perpendicular to the direction of rotation of the rotary part of the gantry.

As shown in FIG. 2, the rotary part 12 rotates on ball bearings 14 relative to the stationary part 13, and a light channel 16 is formed between the rotary part 12 and the stationary part 13. This light channel 16 is formed by a half channel 16*a* in the stationary part 13 and a half channel 16*b* in the rotary part 12. Each of the half channels 16*a* and 16*b* has a parabolic cross-section with a focal point, and each half channel 16*a* and 16*b* also has a vertex. The respective foci and vertices of the half channels 16*a* and 16*b* are co-linear, i.e., they are all disposed on a straight line L. In the embodiment shown in FIG. 2, the half channels 16*a* and 16*b* are disposed relative to each other so that their respective foci coincide at the point designated FP, however, such focal point coincidence is not necessary; it is only necessary for the respective focal points to be co-linear, and to be co-linear with the respective vertices.

Figure 3:
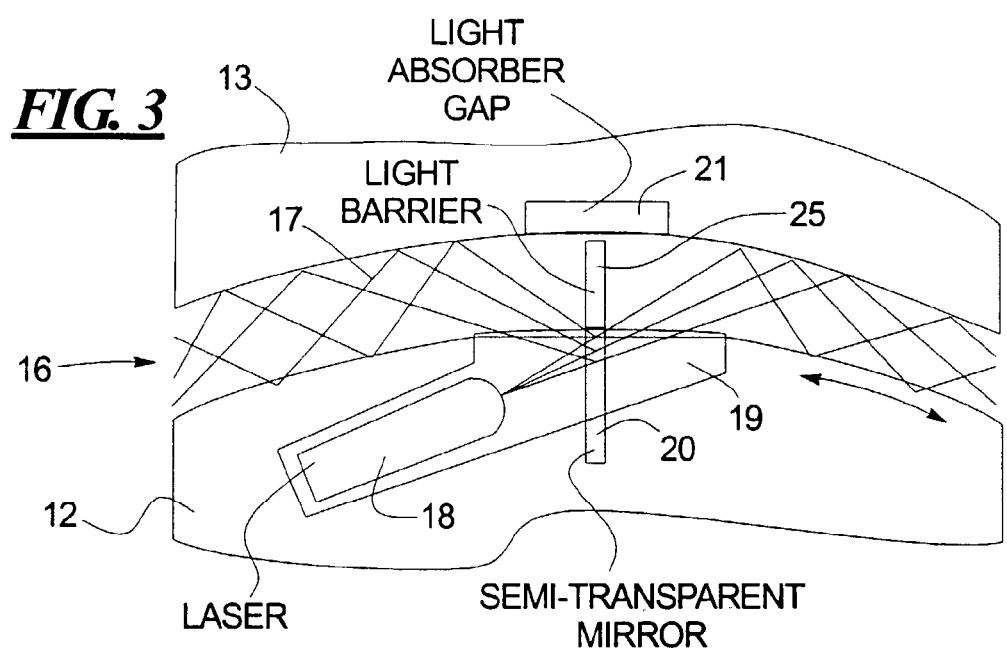
FIG. 3 is a side sectional view through the gantry in the system of FIG. 1, illustrating an embodiment of a light emitter in accordance with the invention.
Figure 4:
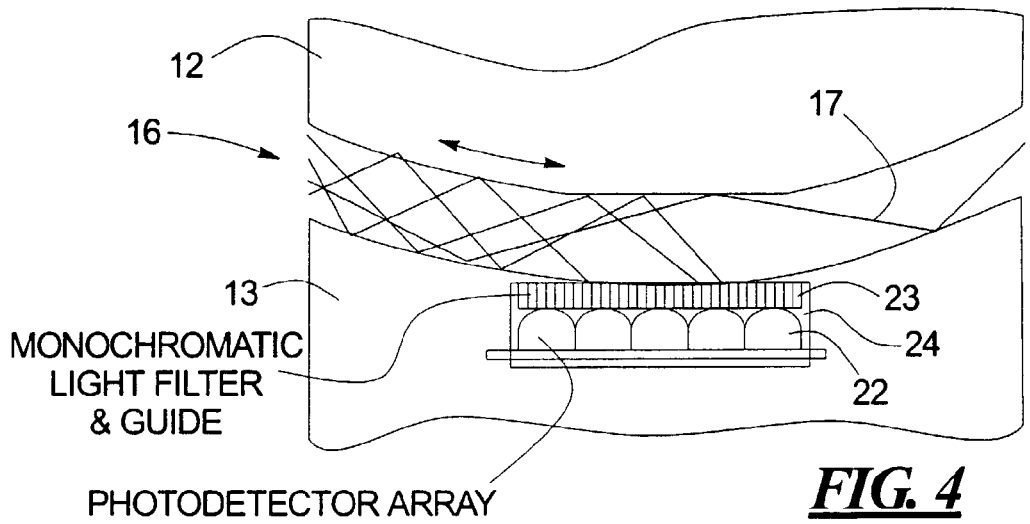
FIG. 4 is a side sectional view through the gantry in the system of FIG. 1, illustrating an embodiment of a light detector in accordance with the invention.

An embodiment of the light emitter is shown in FIG. 3, which emits substantially non-diverging light 17. In this embodiment, the light source is a laser 18, and is disposed in a cavity 19, with walls coated with non-reflective material. The laser 18 is connected by suitable circuitry (now shown) to the output of the radiation receiver so that the emitted light 17 is modulated dependent on the informational content of the output of the radiation receiver 3. The light 17 emitted from the laser 18 propagates in two opposite directions in the light channel 16, by being reflected multiple times at the surfaces of the half channels 16*a* and 16*b*. The oppositely directed light beams are produced by a semi-transparent mirror 20 disposed in the path of the light emitted from the laser 18, The semi-transparent mirror is preferably 50% reflective, so that light beams of approximately equal intensity are produced which are oppositely directed.

FIG. 3 also shows a light absorber gap 21, the purpose of which is described in more detail below.

FIG. 4 shows an embodiment of a light detector, which is disposed in the stationary part 13. In this embodiment, the light detector is formed by a photodetector array 22, preceded a monochromatic light filter and guide 23 tuned to the wavelength of the light 17 emitted by the laser 18. The filter and guide 23 and the photodetector array 22 are disposed in a cavity 24, having walls coated with light-absorbing material.

Figure 5:
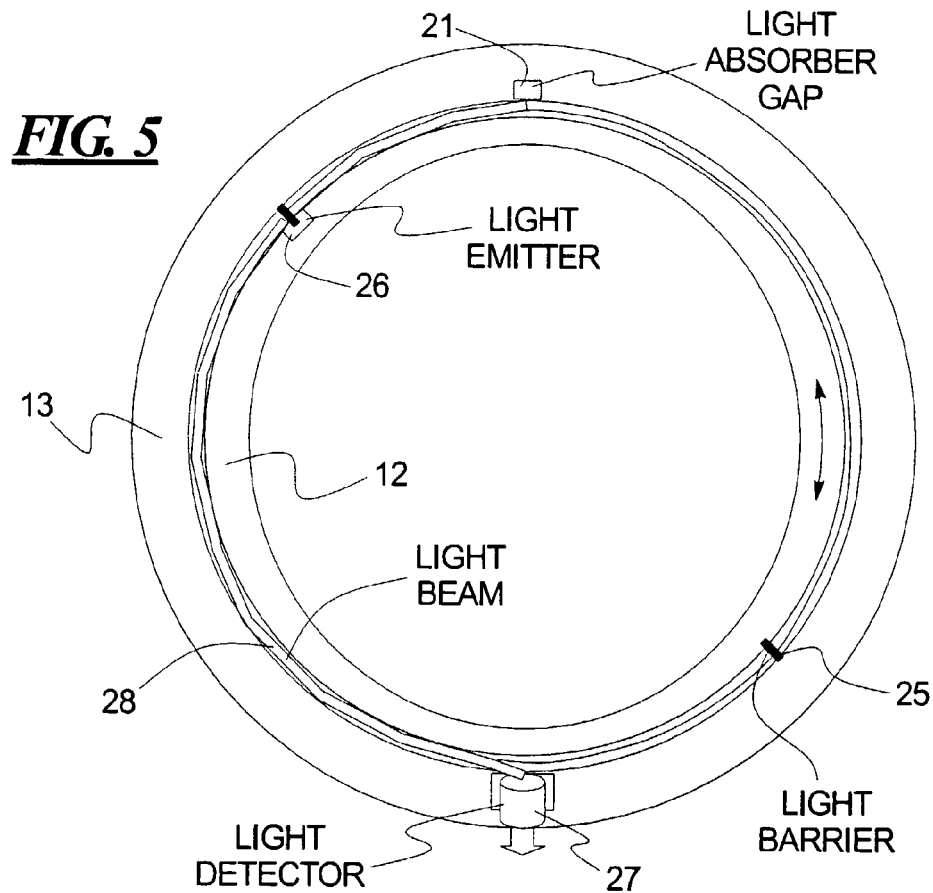
FIG. 5 schematically illustrates the rotary part and the stationary part of the gantry showing the manner by which the light beam propagates in the light channel therebetween, in accordance with the invention.

The basic path of light propagating in the light channel 16 in accordance with the invention is shown schematically in FIG. 5, wherein a light emitter 26 and a light detector 27 are also schematically indicated. The path of the light beam between the light emitter 26 and the light detector 27 is indicated at 28. As can be seen in FIG. 5, although light is emitted in opposite directions from the light emitter 26, only the beam 28 proceeding counterclockwise reaches the light detector 27. The other beam is prevented from reaching the light detector 27 by a light barrier 25. As the rotary part 12 rotates relative to the stationary part 13, therefore, for the most part only one of the two emitted light beams will reach the light detector 27. When the light emitter 26 and the light detector 27 happen to be, during the rotation, oriented at 180° relative to each other, both beams may reach the light detector 27, but the transition in the signal level will be smooth because the light is propagating at that orientation through the same distance in both directions.

As noted above, to minimize mode dispersion the light source that is employed has a small initial dispersion, and the parabolic cross-sectional shape of the light channel 16 controls the propagation path by minimizing light scattering by causing any scattered beams which may arise to be reflected back toward the focal point of the parabola.

Figure 7:
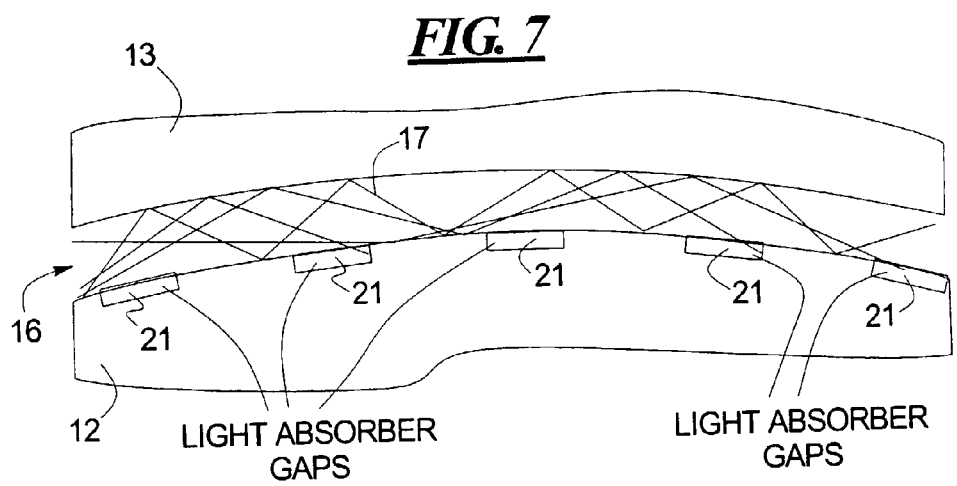
FIG. 7 is a side sectional view through the gantry in the system of FIG. 1, showing how the arrangement of light absorber gaps selects the light propagation modes which are permitted to propagate within the light channel.
Figure 6:
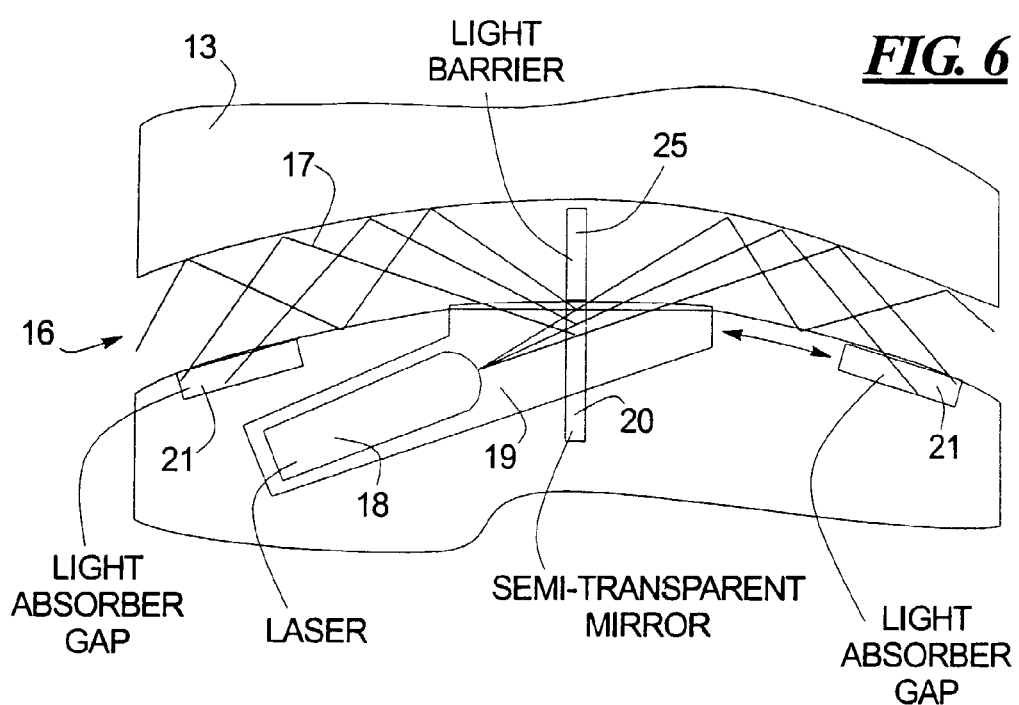
FIG. 6 is a side sectional view of the gantry of FIG. 1, illustrating a further embodiment of the light emitter in accordance with the invention.

To further minimize mode dispersion, a number of light absorber gaps 21 are positioned at locations around the light channel 16, either on the stationary part 13 (as shown in FIG. 3) or on the rotary part 12 (as shown in FIGS. 6 and 7). The light absorber gaps 21 are located at respective positions dependent on the wavelengths of unwanted propagation modes of the light 17, so that light propagating in those modes is absorbed by the light absorber gaps 21. The desired mode or modes then remain, so that mode dispersion is controlled.

The photodetector array 22 may be a two-dimensional array of avalanche photodiodes, connected in parallel to the input of a limiting/AGC amplifier. The gain of this amplifier is automatically adjusted so that the output signal matches the peak-to-peak value of the standard P-ECL (Positive Emitter Coupled Logic) level. The time constant of the gain controlling circuit is set to be large enough to accommodate long sequences of successive zeroes and ones in a bit stream, but small enough to track changes in signal amplitude due to rotation. Using a known modulation method to provide DC balancing, and with conventional gantry rotation speeds, this is simple to achieve.

The free edges of the light barrier 25 may be provided with bristles, so as to remove dust which may accumulate within the channel 16. As can be seen in FIG. 2, although a gap must unavoidably exist between the rotary part 12 and the stationary part 13, covers can be provided at the exterior openings of this gap to assist in keeping the gap free of debris.

Although modifications and changes may be suggested by those skilled in the art, it is in the intention of the inventors to embody within the patent warranted hereon all changes and modifications as reasonably and properly come within the scope of their contribution to the art.

We claim as our invention:

1. A data transmission apparatus comprising:
   a stationary part;
   a rotary part that rotates around an axis relative to said stationary part;
   a data generator mounted on said rotary part;
   a data output on said stationary part at which data generated by said data generator are accessible;
   a circular light channel extending completely around said rotary part, formed by a first optically reflective half-channel in said stationary part and a second optically-reflective half-channel in said rotary part facing toward each other, each of said first and second half-channels having a parabolic cross-section with a focal point and a vertex, the respective foci and vertices being co-linear;
   a light detector disposed in a wall of said first half channel in optical communication with said light channel and in data-transmitting communication with said data output;
   a light emitter which emits two substantially non-diverging light beams modulated to represent said data, respectively propagating in opposite directions in said light channel toward said light detector, said light emitter being disposed in a wall of said second half channel in data-receiving communication with said data generator to receive said data therefrom, and in optical communication with said light channel; and
   a light barrier disposed in said light channel to block one of said two beams so that only one of said two beams is detected at a time by said light detector, except when said light emitter and said light detector are 180° apart.

2. An apparatus as claimed in claim 1 wherein said light emitter comprises a light source which emits a single substantially non-diverging light beam, and a semi-transparent mirror disposed in a path of said single beam to produce said two beams emitted into said light channel.

3. An apparatus as claimed in claim 2 wherein said light source is a laser.

4. An apparatus as claimed in claim 2 wherein said semi-transparent mirror has a transparency of 50%.

5. An apparatus as claimed in claim 2 further comprising a cavity in said rotary part in which said light source and said semi-transparent mirror are disposed, said cavity having cavity walls covered with non-reflective material.

6. An apparatus as claimed in claim 1 wherein said light detector comprises a photodetector array.

7. An apparatus as claimed in claim 6 wherein said photodetector array comprises an array of avalanche photodiodes.

8. An apparatus as claimed in claim 6 wherein said two light beams emitted by said light emitter are monochromatic light beams, and wherein said light detector further comprises a monochromatic light filter disposed in front of said photodetector array, tuned to a wavelength of said monochromatic light beams.

9. An apparatus as claimed in claim 8 wherein said stationary part has a cavity in which said photodetector array and said monochromatic light filter are disposed, said cavity having cavity walls coated with a non-reflective material.

10. An apparatus as claimed in claim 6 wherein said stationary part has a cavity in which said photodetector array is disposed, said cavity having cavity walls coated with a non-reflective material.

11. An apparatus as claimed in claim 1 wherein said two beams exhibit multiple propagation modes, and wherein said apparatus further comprises a plurality of light absorber gaps disposed at respective positions along said light channel, in optical communication with said light channel, said respective positions being relatively spaced from each other to absorb light in said two light beams propagating in at least one of said propagation modes.

12. An apparatus as claimed in claim 1 wherein said stationary part and said rotary part are disposed relative to each other so that said foci coincide.

13. An apparatus as claimed in claim 1 wherein said rotary part is a live ring of a computed tomography apparatus, and wherein said stationary part is frame to which said live ring is rotationally mounted.

14. A method for transmitting data between a rotary part and a stationary part of a system, comprising the steps of:
   forming a circular first optically reflective half-channel, having a parabolic cross-section with a focal point and a vertex, in a stationary part;
   forming a circular second optically reflective half-channel, having a parabolic cross-section with a focal point and a vertex, in a rotary part which rotates relative to said stationary part;
   orienting said first and second half-channels relative to each other, with the respective foci and vertices being co-linear, to form a circular light channel extending completely around said rotary part;
   disposing a light detector in a wall of said first half-channel in optical communication with said light channel and connecting said light detector to a data output at said stationary part;
   disposing a light emitter in a wall of said second half-channel in optical communication with said light channel and supplying data to said light emitter and emitting two substantially non-diverging light beams, modulated to represent said data, from said light emitter into said light channel respectively propagating in opposite directions in said light channel toward said light detector; and
   disposing a barrier in said light channel to block one of said two light beams and thereby causing said light detector to detect only one of said two light beams at a time, except when said light detector and said light emitter are 180° apart.

15. A method as claimed in claim 14 comprising generating said two light beams by emitting a single substantially non-diverging light beam from a light source in said light emitter, and passing said single light beam through a semi-transparent mirror to produce said two light beams emitted into said light channel.

16. A method as claimed in claim 15 comprising providing said semi-transparent mirror with a transparency of 50%.

17. A method as claimed in claim 14 comprising detecting said one of said light beams at said light detector with a photodetector array.

18. A method as claimed in claim 17 comprising forming said photodetector array as an array of avalanche photodiodes.

19. A method as claimed in claim 14 comprising emitting said two light beams as monochromatic light beams, and monochromatically filtering said one of said light beams at said light detector.

20. A method as claimed in claim 14 wherein said two light beams exhibit multiple propagation modes, and comprising the additional step of disposing a plurality of light absorber gaps at respective positions along said light channel, in optical communication with said light channel, and setting relative spacings between said respective positions to absorb light in said two light beams propagating in at least one of said propagation modes.

21. A method as claimed in claim 14 comprising orienting said first and second half channels so that said foci coincide.

22. A method as claimed in claim 14 comprising transmitting data between said light emitter and said light detector, via said two light beams modulated to represent said data, at a data transmission rate of at least 200 MBaud.

23. A method as claimed in claim 14 comprising transmitting data between said light emitter and said light detector, via said two light beams modulated to represent said data, at a data transmission rate of at least 1 GBaud.

* * * * *